US012390527B2

(12) United States Patent
Uspenskij et al.

(10) Patent No.: US 12,390,527 B2
(45) Date of Patent: Aug. 19, 2025

(54) METHOD OF PRODUCING A COMPOSITION FOR BORON NEUTRON CAPTURE THERAPY OF MALIGNANT TUMORS (EMBODIMENTS)

(71) Applicants: MARTIN'EX INTERNATIONAL RESEARCH AND DEVELOPMENT CENTRE (ANO "MNICIT MARTIN'EX"), Moscow (RU); BUDKER INSTITUTE OF NUCLEAR PHYSICS OF SIBERIAN BRANCH OF RUSSIAN ACADEMY OF SCIENCES (BINP SB RAS), Novosibirsk (RU)

(72) Inventors: Sergej Alekseevich Uspenskij, Moscow (RU); Polina Anatol'evna Haptahanova, Elista (RU); Aleksandr Anatol'evich Zaboronok, Minsk (BY); Tihon Sergeevich Kurkin, Troick (RU); Aleksandr Nikolaevich Zeleneckij, Moscow (RU); Mihail Anatol'evich Selyanin, Moscow (RU); Sergej Yur'evich Taskaev, Novosibirsk (RU)

(73) Assignees: MARTIN'EX INTERNATIONAL RESEARCH AND DEVELOPMENT CENTRE (ANO "MNICIT MARTIN'EX"), Moscow (RU); BUDKER INSTITUTE OF NUCLEAR PHYSICS OF SIBERIAN BRANCH OF RUSSIAN ACADEMY OF SCIENCES (BINP SB RAS), Novosibirsk (RU)

( * ) Notice: Subject to any disclaimer, the term of this patent is extended or adjusted under 35 U.S.C. 154(b) by 951 days.

(21) Appl. No.: 17/525,616

(22) Filed: Nov. 12, 2021

(65) Prior Publication Data

US 2022/0062420 A1 Mar. 3, 2022

Related U.S. Application Data

(63) Continuation of application No. PCT/RU2020/000177, filed on Apr. 15, 2020.

(30) Foreign Application Priority Data

Jun. 6, 2019 (RU) ................................. 2019117707

(51) Int. Cl.
*A61K 41/00* (2020.01)
*A61P 35/00* (2006.01)
*A61N 5/10* (2006.01)

(52) U.S. Cl.
CPC .......... *A61K 41/0095* (2013.01); *A61P 35/00* (2018.01); *A61N 5/10* (2013.01); *A61N 2005/109* (2013.01); *A61N 2005/1098* (2013.01)

(58) Field of Classification Search
None
See application file for complete search history.

(56) References Cited

U.S. PATENT DOCUMENTS

2004/0256213 A1   12/2004   Marhasin et al.

FOREIGN PATENT DOCUMENTS

RU   2508963 C2   3/2014
RU   2565432 C1   10/2015

OTHER PUBLICATIONS

Bikramjeet Singh et al., "Nanostructured boron nitride with high water dispersibility for boron neutron capture therapy", Published on Oct. 19, 2016, Scientific Reports, Article No. 35535, pp. 1-10.
Mortensen et al., "Preparation and characterization of Boron carbide nanoparticles for use as a novel agent in T cell-guided boron neutron capture therapy", Applied Radiation and Isotopes, Published in Mar. 2006, vol. 64, Issue 3, pp. 315-324.
Achilli et al.,"Biocompatibility of functionalized boron phosphate (BP04) nanoparticles for boron neutron capture therapy (BNCT) application", Nanomedicine: Nanotechnology, Biology and Medicine, Published on Apr. 2014, vol. 10, N.3, pp. 589-597.
Tiago et al., "An assessment of the potential use of BNNTs for boron neutron capture therapy", Published on Apr. 12, 2017, Nanomaterials 2017, 7(4):82, doi: 10.3390 / nano7040082.

*Primary Examiner* — Michael G. Hartley
*Assistant Examiner* — Samantha L Mejias
(74) *Attorney, Agent, or Firm* — BCF LLP

(57) ABSTRACT

Medical technologies for the creation of target agents for boron-neutron capture therapy of oncological diseases. In a first method variant for preparing a composition for boron neutron capture therapy of malignant tumors containing boron nanoparticles less than 100 nm includes: elemental boron powder being placed in water and treated for 0.5 to 800 minutes with ultrasound with vibration intensity from 1,0 to 1000.0 W/cm³ and the output power greater than 100.0 W. In a second method variant, elemental boron powder is placed in water and treated for 30 to 300 minutes with ultrasound with a same vibration intensity and output power, then the upper part of the composition is taken in a volume less than 50.0 vol. % of total composition volume and treated with ultrasound with vibration intensity from 1.0 to 1000.0 W/cm³ and output power greater than 100.0 W for 250-300 minutes.

18 Claims, 3 Drawing Sheets

Figure 1:
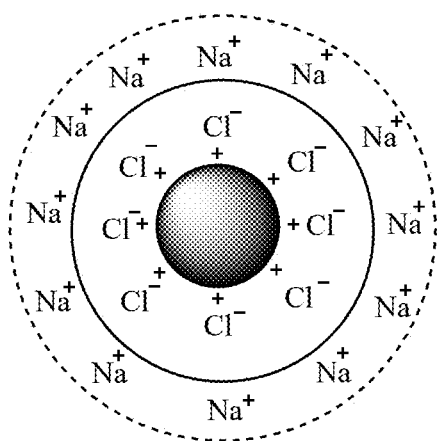

METHOD OF PRODUCING A COMPOSITION FOR BORON NEUTRON CAPTURE THERAPY OF MALIGNANT TUMORS (EMBODIMENTS)

FIELD OF TECHNOLOGY

The group of inventions is related to the field of medical technologies, namely, to the creation of targeting agents for boron neutron capture therapy of oncological diseases, and describes versions of the method of obtaining a composition containing elemental boron nanoparticles.

BACKGROUND

In the present time, the treatment of oncological diseases is a global problem. As a promising approach in the treatment of a number of malignant tumors, first of all, intractable brain tumors, neutron capture therapy is considered, which is extremely attractive by its selective effect directly on malignant tumor cells.

Initially, neutron capture therapy is based on the fact that certain nuclei, such as the stable boron-10 ($^{10}B$) isotope, possess an epithermal/thermal neutron capture cross section several orders of magnitude higher than the carbon, hydrogen, oxygen, and nitrogen atoms that are parts of biological molecules, of which all living cells are built. If substances containing boron-10 isotope are selectively accumulated in a tumor and then irradiated with a flux of epithermal/thermal neutrons, then an intense damage to tumor cells is possible with minimal impact on healthy cells surrounding the tumor. This approach in radiation therapy has acquired the name—boron neutron capture therapy (BNCT).

Neutron capture by a $^{10}B$ nucleus leads to an instant nuclear reaction with the formation of an unstable boron-11 isotope ($^{11}B$), the decay of which leads to the generation of high-energy fission products: an α-particle and a lithium nucleus, characterized by high rates of deceleration and a short path of these particles in water or body tissues—5-10 microns, which is the typical size of mammalian cells. The release of the main part of the $^{10}B$ nuclear reaction energy is limited by the size of one cell. Thus, the selective accumulation of boron-10 inside the affected cells and subsequent irradiation with neutrons should lead to the destruction of tumor cells with relatively little damage to the surrounding normal cells.

One of the main problems of BNCT is the search for target agents that satisfy the main requirement—the content of a large number of boron-10 atoms to achieve a therapeutic concentration in the affected tissues, namely 20.0-35.0 µg per 1.0 g of tumor, which corresponds to ~10 billion boron-10 atoms per 1.0 gram of tumor tissue. Thus, well-known boron-containing drugs used in the clinical BNCT practice—para-boronophenylalanine (BPA) and sodium mercaptododecaborate (Na2B12H11SH)—contain 1 and 12 boron-10 atoms, respectively. Modern boron-containing molecules are compounds of polyhedral boron-10 hydrides with a maximum number of ~26 atoms. To increase the efficiency of the BNCT method, it is necessary to increase the number of target agent atoms in the compound.

The use of elemental boron nanoparticles as an agent for BNCT will significantly increase the efficacy of the drug. With a nanoparticle diameter of 3 nm, the number of boron atoms will be about 120 thousand, and with a diameter of 50 nm—about 2 million atoms.

Currently, methods for boron nanoparticle synthesis by chemical vapor deposition (CVD) are known. The essence of CVD is that isolated nanoparticles are obtained by evaporation of one or more substances containing boron atoms at a controlled temperature in an atmosphere of an inert low-pressure gas, followed by condensation of vapor near or on a cold surface. As a result of the reaction and/or decomposition of the initial substances, boron atoms are released, which lose kinetic energy faster due to collisions with inert gas atoms in a rarefied atmosphere and form segregations (clusters).

There are many ways to implement CVD. Various types of CVD are fundamentally different from each other in the way chemical reactions are triggered and in terms of the process.

For example, electron beam, laser, plasma, arc evaporation methods, or their combinations are used.

The exclusive advantages of CVD methods are the tonnage and one-stage process, as well as a high yield of the target product close to 98% and a high degree of elemental boron purity of 99.6-99.9999%.

The disadvantages of the above methods of preparation should include the fact that they allow for obtaining crystalline powders of elemental boron, in which, micron-sized particles prevail in the powder as a result of the sintering process, that makes it difficult to use them as agents in BNCT, since boron-containing compounds should be used in the form of solutions or suspensions (preferably the size of solid particles should not be more than 50-70 nm), injected with a syringe.

Modern ultrasonic (US) technologies are a new approach to solve various technological problems of modern industries. The "Nano-Size" company on the basis of an ultrasonic system with a power of 4.0±0.05 kW has created a sonochemical reactor (US 20040256213 A1, Dec. 23, 2004) for the production of nanoparticles. To prepare nano-sized metal oxides and hydroxides, a solution of a metal salt (usually a chloride) in a suitable solvent is exposed to a high-power ultrasound in the presence of a base such as an alkali metal hydroxide, for example. According to the well-known solution, a ten-liter reactor providing an intensity of ultrasonic vibrations of 0.6 W/cm$^3$ is suitable for such purposes (moreover, the authors emphasize that it is a magnetostrictive transducer which is used). Under these conditions, highly active radicals are created inside the rapidly exploding cavitation bubbles, founding the nuclei of nanoparticles. In such a sonochemical reaction, a solution of one mole of a metal salt provides up to several hundred grams of a nano-product with sizes from 5 to 60 nm in a short time (about 3-6 minutes).

Examples of compounds out of which nanoparticles can be obtained by that approach are oxides: FeO, Fe2O3, Fe$_3$O$_4$, NiO, Ni2O3, CuO, Cu2O, Ag2O, CoO, Co2O3, and crystal hydrates: Fe(OH)3, Co(OH)3, NiO(OH), BaTiO3. Metal nanoparticles can also be obtained by that known method, for example Fe, Co, Cu, Ag, Ni, Pd nanoparticles. Such a reactor is an effective device for accelerating chemical reactions. For example, the transformation of metal salts or oxides into metal powder in relatively large amounts (1.0 mol) is completed within 5-10 minutes. Such a powder consists of ultrafine metallic or non-metallic particles in the nanoscale range of 5-100 nm.

In the US 20040256213 A1 document, the formation of metal nanoparticles occurs primarily as a result of a redox reaction, where the chemical synthesis is based on the reduction of metal ions to atoms, followed by the aggregation of atoms to form clusters. The aggregation of clusters leads to the formation of metal nanoparticles. Aggregates of clusters are characterized by a weak van der Waals interaction, they are unstable. Ultrasonic dispersion temporarily helps to prevent the formation of agglomerates, facilitates their destruction to the original metal clusters.

A method of dispersing nanosized silica powder by ultrasound is also known (patent RU 2508963, Mar. 10, 2014). The method implies the placement of Tarkosil T05B06 silicon dioxide nanopowder into the liquid and exposure to ultrasonic vibrations for 3 minutes, ensuring the acoustic cavitation mode in the treated medium at a resonant frequency of 23.0 kHz. The power of the ultrasonic unit is 0.63 kW. The average nanoparticle size is 53 nm. However, this method is not applicable to create a composition containing boron nanoparticles, and the composition obtained by this method is not applicable in boron neutron capture therapy.

From the level of technology an RF patent No. 2565432, published on Oct. 20, 2015, is known, which discloses a method for producing boron nitride nanoparticles as carriers of an antitumor agent for the delivery to affected cells. The method is characterized by the fact that spherical boron nitride nanoparticles 50-300 nm in size with a developed outer surface are synthesized by a CVD method using reaction and transport gases, as well as powder mixtures consisting of amorphous boron and reagent-oxidizing agents, and then the agglomerates of the resulting boron nitride nanoparticles are dispersed by ultrasonic processing, boron nitride nanoparticles are saturated with an anticancer agent by sorption, and the nanoparticles are washed in distilled water. Boron nitride nanosized structures have the ability to penetrate into tumor cells by means of endocytosis and release the therapeutic substance particularly into the perinuclear region. This method allows for improving the efficacy of antitumor chemotherapy by increasing the activity of absorption of the nanocontainers with an antitumor drug by cells and preventing toxicity of the nanocontainers for the cells.

The proposed method is initially focused on obtaining boron nitride nanoparticles. Boron nitride is a binary compound of boron and nitrogen BN; the boron content in a boron nitride nanoparticle is two times less than in nanoparticles consisting only of elemental boron.

Boron nitride particles are resistant to oxidation. Boron nitride is oxidized by oxygen at temperatures above 700° C., has chemical resistance and decomposes in hot alkali solutions with the release of ammonia. Boron nitride nanoparticles are not completely eliminated from the human body and can accumulate in organs and tissues. The inert surface of boron nitride particles complicates further modification/functionalization of their surface to impart properties that determine the use in targeted therapy.

In the work [Tiago H. Ferreira et al., An assessment of the potential use of BNNTs for boron neutron capture therapy// Nanomaterials 2017, 7, 82; doi: 10.3390/nano7040082], the effectiveness and fundamental applicability of boron nitride nanoparticles in the treatment of malignant tumors is shown. Thermal neutron flux in combination with large boron amounts internalization contributes to a significant amount of cell death. However, the authors do not mention that at the moment of thermal neutron reaction with boron nitride nanoparticles, not only the boron-10, but also the nitrogen-14 isotope is activated. As a result, transmutational transformations of nitrogen with the formation of a highly radioactive carbon-14 isotope occur according to the reaction:

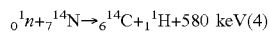

$$_0^1 n + _7^{14}N \rightarrow _6^{14}C + _1^1H + 580 \text{ keV} \quad (4)$$

The lower the neutron speed, the higher the probability of occurring of the nuclear reaction. Carbon-14 isotope decays with the release of 0.158 MeV of energy and dangerous for humans 0-radiation. Radioactive carbon-14 is used in medicine as a radioactive tracer. However, recently, efforts are made to replace the test based on $^{14}C$ atom-labelling with a test with stable $^{13}C$, which is not associated with radiation risks. The half-life of carbon-14 is 5730 years.

Elemental boron nanoparticles can be oxidized. For example, the interaction of boron with hydrogen peroxide. In mammals, some enzyme systems (xanthine oxidase, NADPH-oxidase, cyclooxygenase, etc.) produce superoxide, which is converted spontaneously or under the action of superoxide dismutase into hydrogen peroxide. Boron oxidation rate depends on crystallinity, particle size, purity and temperature. Boron is oxidized to form oxides. Boron oxide reacts with water to form boric acid, which is relatively harmless to the body. Thus, boron nanoparticles can be used in medicine, particularly in cancer therapy, without fear of the side effects traditionally associated with such therapies.

Considering the above, the use of compositions containing elemental boron nanoparticles in BNCT is the most acceptable and safe.

Thus, from the technology level there are no known methods to synthesize compositions for boron neutron capture therapy of malignant tumors containing boron nanoparticles less than 100 nm in size.

SUMMARY

The objective of the proposed group of inventions is to create environmentally friendly, fundamentally new variants of a method of preparing a composition for boron-neutron capture therapy of malignant tumors containing boron nanoparticles less than 100 nm in size.

The technical result of the proposed group of inventions is to obtain compositions for boron-neutron capture therapy of malignant tumors with a high content of boron nanoparticles stable in time.

To solve the problem and obtain the technical result, variants of the method for producing a composition for boron neutron capture therapy of malignant tumors are proposed.

According to the first non-limiting embodiment, a method for preparing a composition for boron neutron capture therapy of malignant tumors containing boron nanoparticles less than 100 nm in size includes the following steps: elemental boron powder is placed in water and treated with ultrasound for 0.5 to 800 minutes with an intensity of vibration from 1.0 to 1000.0 W/cm$^3$ and an output power of more than 100.0 W.

According to the second non-limiting embodiment, the method for preparing a composition for boron neutron capture therapy of malignant tumors containing boron nanoparticles less than 100 nm in size includes the following steps: the elemental boron powder is placed in water and treated for 30 to 300 minutes with ultrasound with an intensity of vibration from 1.0 to 1000.0 W/cm$^3$ and an output power of more than 100.0 W, then the upper part of the composition is taken in a volume of less than 50 vol. % of the total volume of the composition and this part is treated with ultrasound with an intensity of vibration from 1.0 to 1000.0 W/cm$^3$ and an output power of more than 100.0 W for 250-300 minutes.

In any of the above options, it is possible, before sonication or during sonication, to add to the composition a water-soluble inorganic metal salt with an oxidation state of +1 or a mixture of such salts. Moreover, chlorides, nitrates, sulfates, sulfites, preferably chlorides of the metals: sodium, potassium, lithium, are used as water-soluble inorganic metal salts with an oxidation state of +1.

In the final composition, stabilizers can be further added, such as: suitable for injection in the human body organic metal salts (for example, citric or acetic acid salts) or their mixtures and/or inorganic metal salts with an oxidation state equal to or greater than +2, and/or compounds selected from the following group: blood plasma proteins, antibodies, hormones, E400-E499 additives and/or their base substances of pharmacopoeial purity, polysaccharides, fatty acids, plant proteins, amino acid derivatives: 1-amino-3-cyclobutane-1-carboxylic acid and 1-amino-3-cyclopentanecarboxylic acid derivatives, phenylalanine, linear and cyclic peptides, purines, pyrimidines, thymidines, nucleosides and nucleotides: 3-carboranyl thymidine analogs, porphyrins, pluronics, polyhydric alcohols, polyethylene glycol, polyvinylpyrrolidone, polyvinyl alcohol, synthetic polyamino acids.

Acetates or citrates are also used as stabilizers—salts or esters of acetic and citric acids (for example, acetates or citrates of such metals as magnesium, aluminum, calcium, scandium, titanium, vanadium, chromium, manganese, iron, cobalt, nickel, copper, zinc, gallium, germanium, arsenic, rubidium, strontium, iridium, niobium, molybdenum, ruthenium, rhodium, palladium, silver, cadmium, gold).

The mass ratio of boron to salt or to a mixture of salts is in the range from 1:0.01 to 1:30.0.

As an elemental boron powder, in any of the variants, amorphous boron powder or coarse-crystalline boron powder or fine-crystalline boron powder or their mixtures are used.

DETAILED DESCRIPTION

The method of obtaining boron nanoparticles involves the use of ultrasonic equipment with high-intensity vibrations, as well as that with an output power in the range over 100.0 W. The capabilities of ultrasonic vibrations during the intensification of technological processes in liquid media are realized through the contact application of ultrasonic vibrations directly to the liquid media containing microparticles of elemental boron, and in creating conditions for the development and maintenance of the cavitation mode. Cavitation is the main destruction factor, which is an effective mechanism of energy concentration. Cavitation begins when certain vibration intensity thresholds are exceeded from 1.0 W/cm$^3$ to 1000.0 W/cm$^3$ at atmosphere pressure and room temperature. With changes in pressure, temperature and exposure time, cavitation can begin at a lower power. A powerful sound field in a liquid generates small vapor-gas bubbles, which, under the influence of this field, can grow and collapse. The total energy of the collapsing bubble is small, but the spherical convergence of the bubble leads to the formation of very high local energy densities, and, consequently, high temperatures of 5000-25000 K and pressures of 100 MPa. Under the influence of such loads, dispersion/destruction of large crystallites of the initial elemental boron powder and the formation of nanosized particles less than 100 nm in size occur. The concentration of boron nanoparticles, as well as their size, depend on the time of the cavitation impact on the liquid composition (from 0.5 to 800 min) and on the output power of the ultrasonic equipment (over 100 W). The concentration of boron nanoparticles in the liquid medium varies in the range from 0.0001 wt % to 30 wt %.

The use of water (bidistilled or distilled) as one of the components of the composition is one of the main advantages, since the final form of the compound for BNCT is presented in the form of an aqueous dispersion of elemental boron nanoparticles, in contrast to traditional methods of nanoparticle synthesis, where they are obtained in the form of a sintered powder.

Ultrasonic processing leads to the formation of boron nanoparticles with an active surface that interacts with water. The authors determined the positive ξ-potential of particles after cavitation. To increase the shelf life of a composition without losing its original properties, the resulting compositions must be stabilized—this will reduce their agglomeration for a long time and preserve the dimensional properties of the particles. The presence of a charge on the surface of a particle is a prerequisite for its functionalization, since it allows particles to adsorb ions from solution on their surface. As a result, an adsorption layer is formed, consisting of potential-determining ions and counterions, and a diffuse layer containing residual counterions.

To increase the aggregate stability of boron nanoparticles, ultrasonic cavitation processing is carried out in the presence of metal salts, which additionally contribute to co-grinding (the speed of the liquid stream reaches 400 km/h, Mason 1989; Hielscher 2005) and act as re-dispersing components. Ultrasonic influence of high energy and the presence of re-dispersing components in the system will contribute to the controlled destruction of the elemental boron structure and, at the same time, the matrix isolation of the new structure—the formation of a new particle or micelle, which core is a boron nanoparticle, and the stabilizing shell, for example, is Na+ and Cl− (FIG. 1).

At least one stabilizing additive can be added to the reaction mixture-dispersion of boron nanoparticles in water. The stabilizing additives are low molecular weight and/or oligomeric compounds (the number of repeating units n ranges from 10 to 100), as well as high molecular weight compounds (n>100), which help to reduce the degree of aggregation, thereby stabilizing boron nanoparticles, which can be carried out at different stages of particle synthesis: the addition of a stabilizer at different stages of cavitation or its placement into the final composition in the form of liquid (liquid phase). Particle stabilization occurs due to passive adsorption of low molecular weight salts and/or oligomer/polymer on the particle surface, or due to the high viscosity of their solutions.

A developing method of stabilization is the use of oligomers and/or high molecular weight compounds, which solutions have high viscosity. As a result of this stabilization, called steric, the nanoparticles will be surrounded by a protective barrier, which is a continuous layer of solvated polymer chains, as a result of which the colloidal system becomes indefinitely stable as long as the protective layer remains intact. The use of an oligomer and/or polymer as a stabilizer leads to an increase in kinetic stability due to an increase in the viscosity of the colloid with boron nanoparticles. Molecules of biological origin are used as oligomers and/or high molecular weight compounds for stabilization. For example, blood plasma proteins, antibodies, hormones.

Auxiliary stabilizers are also used, for example, E400-E499 additives and/or their main substances of pharmacopoeial purity (quality); polysaccharides; fatty acids; vegetable proteins; amino acid derivatives: 1-amino-3-cyclobutane-1-carboxylic acid and 1-amino-3-cyclopentanecarboxylic acid; linear and cyclic peptides; purines, pyrimidines, thymidines, nucleosides and nucleotides: 3-carboranyl thymidine analogs; porphyrins. Pluronics, polyhydric alcohols, polyethylene glycol, polyvinylpyrrolidone, polyvinyl alcohol, and synthetic polyamino acids are also used.

Boron isotopes can be used as elemental boron in the form of a powder: boron-10, boron-11 or their mixture in the form of an amorphous, coarse-crystalline and fine-crystalline powder or their mixtures. It is preferable to use boron-10 isotope, where the content of the main component is more than 99%.

A magnetostrictive, piezoelectric transducer is used as a device that creates cavitation. In all cases, the ultrasonic device converts electrical power into vibrational energy using a transducer that changes its size in response to an applied alternating current electric field.

According to the literature data, elemental boron forms several allotropic modifications (see Table 1), which differ in the structure of the crystals. In this case, the matrix of crystals is the energetically stable icosahedral structure of B12. The formation of this or that modification is determined by the technological method of obtaining elemental boron. A mixture of various modifications can be obtained simultaneously.

Under high pressure and temperature arising from the collapse of cavitation bubbles in an ultrasonic field at the phase boundary, elemental boron is destroyed. As a result of such impact, the destruction of amorphous regions of elemental boron and the formation of a new molecular system occur simultaneously by the mechanism of small clusters assembling into high-dimensional nanosystems.

TABLE 1

| Allotropic boron modification | α-R | α-T | β-R | β-T | γ | Amorphous Powder | Amorphous Compressed powder |
|---|---|---|---|---|---|---|---|
| Symmetry | Rhombo-hedral | Tetragonal | Rhombo-hedral | Tetragonal | Ortho-rhombic | Random | Random |
| Number of atoms | 12 | 50 | 105-108 | 192 | 28 | | |
| Density (g/cm2) | 2.46 | 2.29-2.39 | 2.35 | 2.36 | 2.52 | 1.73 | 2.34-2.35 |
| Vickers hardness (GPa) | 42 | 45 | 50-58 | | | | |
| Volumetric modulus (GPa) | 224 | 184 | 227 | | | | |
| Color | White | Black with a pronounced metallic sheen | Gray | Black/red | Gray | Brown | Black |

The size and shape of boron particles were studied using methods such as dynamic light scattering and electron microscopy. The size distribution of nanoparticles was calculated in the automatic DLS mode and on the basis of the obtained micrographs using ImageJ 1.48v software.

The invention is illustrated by figures.

FIG. 1—the example of boron nanoparticles stabilization with sodium chloride.

Figure 2:
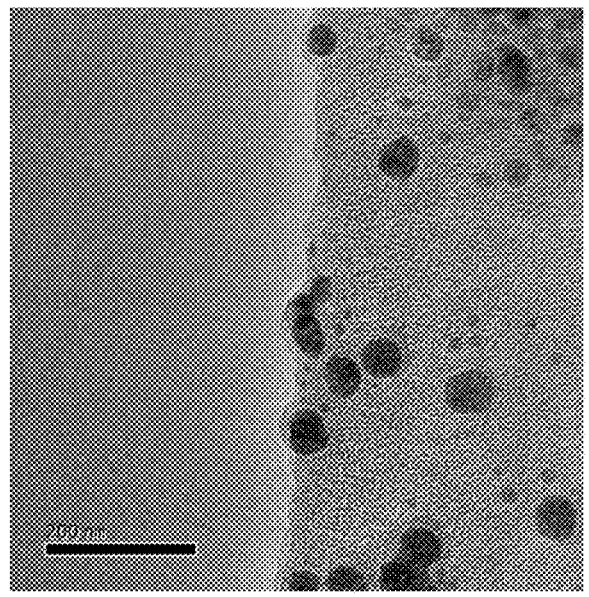

FIG. 2—micrographs of boron nanoparticles with a size of 20-50 nm at a magnification of ×35000.

Figure 3:
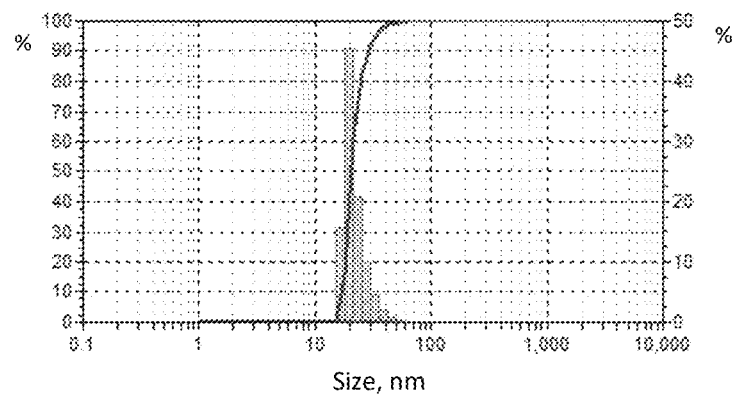

FIG. 3—boron particle size distribution diagram: 20 nm—30%; 35 nm—45%; 40 nm –15%; 50 nm—10%.

Figure 4:
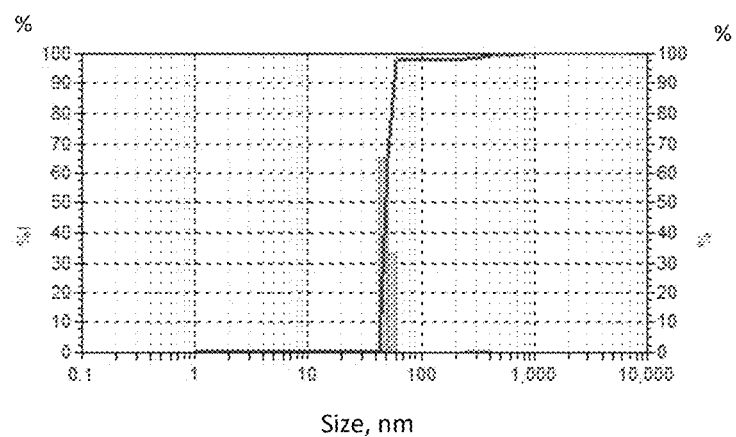

FIG. 4—boron particle size distribution diagram: 20 nm—70%; 40 nm—30%.

Figure 5:
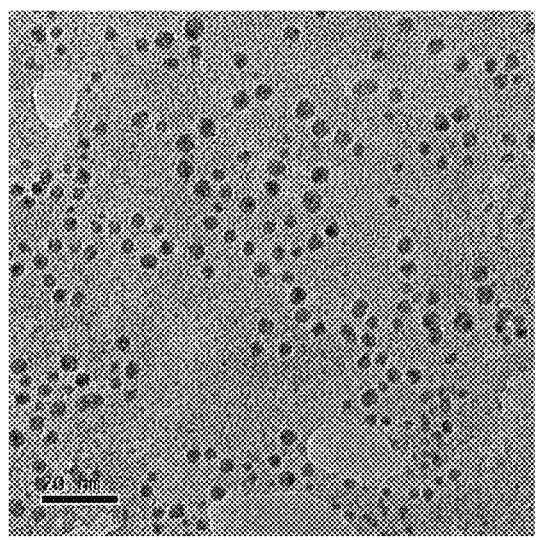

FIG. 5—micrographs of boron nanoparticles with a size of 5-20 nm at a magnification of ×45000.

Figure 6:
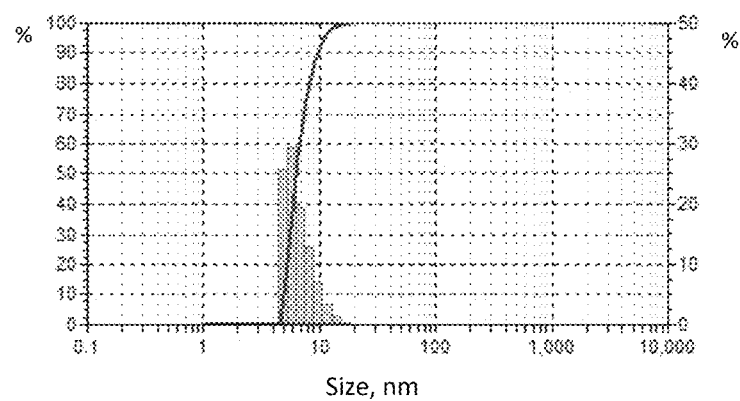

FIG. 6—boron particle size distribution diagram: 4 nm—30%; 8 nm—40%; 10 nm—15%; 15 nm—15%.

Figure 7:
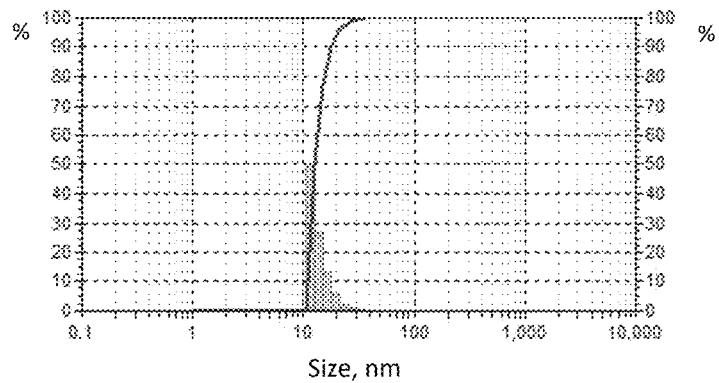

FIG. 7—boron particle size distribution diagram: 10 nm—50%; 16 nm—30%; 20 nm –20%.

With prolonged exposure to ultrasound of different powers, the most effective particle size reduction and at the same time their ovalization or spheroidization occur (FIG. 2, FIG. 4). At the same time, the monodispersity and the content of spherical particles increase up to 90-100%. The invention can be illustrated by the following examples.

Example 1. 5.0 g of amorphous elemental boron powder is added to 25.0 ml of bi-/distilled water. The initial boron concentration is 20.0 wt % or 190.0-200.0 mg/ml. The initial particle size varies from 0.4 to 2.0 microns. A micron dispersion of elemental boron in water is exposed to ultrasound for 200 minutes. The process is carried out using ultrasonic equipment with an output power of 1.5±0.05 kW, with an intensity of ultrasonic vibrations from 1.5 to 3.0 W/cm$^3$. The obtained composition contains nanoparticles (NPs) with a size of 50 nm, with nanoparticle concentration of 170.0-180.0 mg/ml in H$_2$O. The surface charge of boron nanoparticles is positive. The value of the ξ potential is +13. The shape of the particles is irregular with sharpened edges. The stability of the composition over time is not more than 96 hours.

Example 2. Performed similarly to the example 1, however, in contrast to it, ultrasonic equipment with an output power of 4.0±0.05 kW, with an intensity of ultrasonic vibrations from 4.0 to 8.0 W/cm$^3$ was used. The exposure time to the initial dispersion of boron particles in water is 200 minutes—a composition containing nanoparticles of 20 nm in size with a concentration of 170.0-180.0 mg/ml in H$_2$O is obtained. The surface charge of boron nanoparticles is positive. The value of the ξ potential is +10. The shape of the particles is spherical. The stability of the composition in time is not more than 96 hours.

Example 3. Performed similarly to the example 1, however, in contrast to it, ultrasonic equipment with an output power of 25.0±0.05 kW, with an intensity of ultrasonic vibrations from 25.0 to 35.0 W/cm$^3$ was used. The exposure time to the initial dispersion of boron particles in water is 70 minutes—a composition containing nanoparticles <5 nm in size with a concentration of 170.0-180.0 mg/ml in H$_2$O is obtained. The surface charge of boron nanoparticles is positive. The value of the ξ potential is +5. The shape of the particles is spherical. The stability of the composition in time is not more than 96 hours.

Example 4. Performed similarly to the example 2, however, in contrast to it, the exposure time to the initial micron dispersion of boron particles in water was 350 minutes—a composition was obtained containing nanoparticles with a size of 10±5 nm, with a concentration of 170.0-180.0 mg/ml in H$_2$O. The surface charge of boron nanoparticles is positive. The value of the ξ-potential is +8. The shape of the particles is spherical. The stability of the composition in time is not more than 96 hours.

Example 5. Performed similarly to the example 4. In this case, before sonication, sodium chloride is placed into the mixture in the mass ratio (boron):(NaCl)=1:10, while the salt concentration is 0.9% (this percentage fits the range of acceptable concentrations of the saline solution for administration into the human body). After complete dissolution of sodium chloride in water during 3 minutes, the analyzed solution is exposed to ultrasound for 350 minutes. A stabilized composition containing nanoparticles with a size of 20±5 nm is obtained, with nanoparticle concentration of 170.0-180.0 mg/ml in H$_2$O. The surface charge of boron nanoparticles is neutral. The value of ξ-potential is not less than +60. The shape of the particles is spherical. The stability of the composition over time is 3 months.

Example 6. Performed similarly to the example 4. In this case, before sonication, sodium chloride is placed into the mixture in the mass ratio (boron):(NaCl)=1:20, while the salt concentration is 0.9% (this percentage fits the range of acceptable concentrations of the saline solution for administration into the human body). After complete dissolution of sodium chloride in water during 3 minutes, the analyzed solution was subsequently exposed to ultrasound. The stabilized composition containing nanoparticles with a size of 8±5 nm was obtained, with nanoparticle concentration of 170.0-180.0 mg/ml in H$_2$O. The surface charge of boron nanoparticles is neutral. The value of ξ-potential is not less than +65. The shape of the particles is spherical. The stability of the composition over time is more than 1 year.

Example 7. Performed similarly to the example 6, but in contrast to it, the stabilizing system KCl—LiCl was used in the mass ratio (nanoparticles):(KCl—LiC)=1:23. The mass of the initial micron powder was 10.0 g per 25.0 ml of H$_2$O. The initial boron concentration was 40.0 wt % or 390.0-400.0 mg/ml. The concentration of the salt mixture was 0.9% (this percentage fits the range of acceptable concentrations of the saline solution for administration into the human body). After complete dissolution of sodium chloride in water for 3 minutes, the analyzed solution was subsequently exposed to ultrasound. The stabilized composition containing nanoparticles with a size of 10±5 nm was obtained, with nanoparticle concentration of 390.0-400.0 mg/ml in H$_2$O. The surface charge of boron nanoparticles is neutral. The value of the ξ-potential is not less than +59. The shape of the particles is spherical. The stability of the composition overtime is more than 2 years.

Example 8. Performed similarly to the example 6, but in contrast to it, the sodium citrate was used as a stabilizer, in the mass ratio (nanoparticles) (Na3C6H5O7)=1:20. The mass of the initial micron powder was 10.0 g per 25.0 ml of H$_2$O. The initial boron concentration was 40.0 wt %, or 390.0-400.0 mg/ml. After complete dissolution of sodium citrate in water for 3 minutes, the analyzed solution was subsequently exposed to ultrasound. The stabilized composition containing nanoparticles with a size of 8±5 nm was obtained, with nanoparticle concentration of 390.0-400.0 mg/ml in H$_2$O. The surface charge of boron nanoparticles is neutral. The ξ-potential value is not less than +50. The shape of the particles is spherical. The stability of the composition over time is more than 1 year.

Example 9. Performed similarly to the example 6, but in contrast to it, sodium acetate was used as a stabilizer, in the mass ratio (nanoparticles):(Na3C6H5O7)=1:25. The mass of the initial micron powder was 10.0 g per 25.0 ml of H$_2$O. The initial boron concentration was 40.0 wt % or 390.0-400.0 mg/ml. After complete dissolution of sodium acetate in water during 3 minutes, the analyzed solution was subsequently exposed to ultrasound. The stabilized composition containing nanoparticles with a size of 12±5 nm was obtained, with nanoparticle concentration of 390.0-400.0 mg/ml in H$_2$O. The surface charge of boron nanoparticles is neutral. The value of 4-potential is not less than +55. The shape of the particles is spherical. The stability of the composition over time is more than 1 year.

Example 10. Performed similarly to the example 6, however, in contrast to it, a high-molecular compound, carboxymethylcellulose, with a molecular weight of 220 kDa was used as a stabilizer. The composition containing boron nanoparticles was poured into the carboxymethyl cellulose solution with stirring for complete distribution of the particles in the matrix of the high molecular weight stabilizer. It was found that the use of an aqueous solution of carboxymethylcellulose with a concentration of 2% to 5% is optimal, since the viscosity of the solution is significantly increased, but it does not have a gel structure. The surface charge of the boron nanoparticles is neutral; the value of ξ-potential+65; the shape of the particles is spherical; the stability time of the obtained composition is more than 3 years.

Example 11. Performed similarly to the example 6, however, in contrast to it, a powder of coarse-crystalline elemental boron was used, with an initial particle size of 0.5-1.0 microns. The time of exposure of the initial micron dispersion of coarse-crystalline boron particles to ultrasound in the presence of NaCl was 350 minutes—the obtained composition contained nanoparticles with a size of ≈100 nm; the concentration of nanoparticles is 170.0-180.0 mg/ml in H$_2$O; the surface charge of boron nanoparticles is neutral; the value of ξ-potential from +50; the shape of the nanoparticles is spherical; the stability of the composition over time is more than 1 year.

Example 12. Performed similarly to the example 11, however, in contrast to it, the exposure time on the dispersion of boron particles in water was 600 minutes—a composition containing nanoparticles with a size of 5±3 nm was obtained, with nanoparticle concentration of 170.0-180.0 mg/ml in H$_2$O. The surface charge of boron nanoparticles is neutral. The value of the ξ-potential is +60. The shape of the particles is spherical. The stability of the composition over time is more than 1 year.

Example 13. Performed similarly to the example 6, however, in contrast to it, a fine-crystalline elemental boron powder was used, with an initial particle size of 0.4-1.2 microns. The time of exposure of the initial micron dispersion of fine-crystalline boron particles to ultrasound in water in the presence of NaCl was 350 minutes—a composition was obtained containing nanoparticles with a size of ≈80 nm; concentration of nanoparticles was 170.0-180.0 mg/ml in H$_2$O; the surface charge of boron nanoparticles is neutral; the value ξ-potential starts from +68; the shape of the nanoparticles is spherical; the stability of the composition over time is more than 1 year.

Example 14. Performed similarly to the example 13, however, in contrast to it, the exposure time to the dispersion of boron particles in water was 500 minutes—a composition containing nanoparticles with a size of 10±5 nm was obtained, with a concentration of 170.0-180.0 mg/ml in H$_2$O. The surface charge of boron nanoparticles is neutral. The value of the ξ-potential is +70. The shape of the particles is spherical. The stability of the composition over time is more than 1 year.

Example 15. 5.0 g of powdered amorphous boron was added to 25.0 ml of bi-/distilled water. The initial boron concentration was 20.0 wt %, or 190.0-200.0 mg/ml. The initial particle size was 0.5-2.0 microns. The process was carried out using ultrasonic equipment with an output power of 4.0±0.5 kW, with an intensity of ultrasonic vibrations of 4.0-8.0 W/cm$^3$. The time of exposure of the elemental boron particles dispersion to ultrasound in water was 200 minutes. Then upper part is taken. The volume of the sampled part is approximately 50.0 vol. % of the total volume of the system. The size of the boron particles in the sampled portion is 50 nm. The selected part is re-exposed to ultrasound for 200 minutes. As a result, the composition containing nanoparticles with a size of 5±1 nm was obtained, with nanoparticle concentration of 85.0-90.0 mg/ml in H$_2$O. The surface charge of boron nanoparticles is positive. The value of ξ-potential is from +6. The shape of the particles is spherical. The stability time is no more than 96 hours. The remaining part, about 50.0 vol %, is concentrated for subsequent sonication.

Example 16. Performed similarly to the example 15, however, in contrast to it, the volume of the taken dispersion after 200 minutes of sonication was approximately 10.0% of the total volume of the system. The size of boron particles in the sampled portion is 50 nm. The selected part is re-exposed to ultrasound for 200 minutes. The result is a composition containing nanoparticles with a size of 2-5 nm, with nanoparticle concentration of 17.0-18.0 mg/ml in H$_2$O. The surface charge of boron nanoparticles is positive. The value of ξ-potential is from +2. The shape of the particles is spherical. The stability in time is not more than 96 hours. The remaining part, about 90.0 vol. %, is concentrated for subsequent sonication.

Example 17. To assess the parameter of boron nanopowder redispersion, the selected dispersion of particles (50 nm) in water concentrated to approximately 55.0 vol. % (or 90.0 vol. %) was used to obtain boron nanoparticles with a size of less than 10 nm for each type of boron. Obtaining of particles nanodispersion was carried out similarly to the examples 13-14. After obtaining nanoparticles in water with the required size (≈10 nm), the dispersion was concentrated by freeze drying in a vacuum. After obtaining boron nanoparticles in the form of a powder, the redispersion process was carried out as follows: 3.0 g, or 12.0 wt %, of boron nanoparticle powder was added to 10.0 ml of bi-/distilled water; exposed to ultrasound of various powers for 2 minutes. The dimensional properties of the nanoparticles are preserved.

Example 18. Sodium chloride is added to the composition with boron nanoparticles obtained as indicated in example 17 in a mass ratio (nanoparticles):(NaCl)=1:20, while the salt concentration is 0.9% (this percentage fits the range of acceptable concentrations of the saline solution for administration into the human body). After complete dissolution of sodium chloride in water during 3 minutes, the analyzed solution was again exposed to ultrasound for 2 minutes. The stabilized composition containing nanoparticles with a size of ≈10 nm was obtained, with nanoparticle concentration of 85.0-90.0 mg/ml (or 17-18 mg/ml) in H$_2$O. The surface charge of boron nanoparticles is neutral. The value of ξ-potential is more than +55. The shape of the particles is spherical. The stability of the composition over time was confirmed for more than 2 years.

Example 19. 5.0 g of amorphous elemental boron powder was added to 25.0 ml of bi-/distilled water. The initial boron concentration was 20.0 wt % or 190.0-200.0 mg/ml. The initial particle size was from 0.4 to 2.0 microns. The micron dispersion of elemental boron in water was exposed to ultrasound for 600 minutes. The process is carried out using ultrasonic equipment with an output power of 0.3±0.03 kW and the ultrasonic vibration intensity from 1 to 1.5 W/cm$^3$. The obtained composition contains particles less than 100 nm in size, with a concentration of 170.0-185.0 mg/ml of nanoparticles in H$_2$O. The surface charge of boron nanoparticles is positive. The value of the ξ-potential is +21. The shape of the particles is irregular with sharpened edges. The stability of the composition in time is less than 96 hours.

Example 20. 5.0 g of amorphous elemental boron powder is added to 25.0 ml of bi-/distilled water. The initial boron concentration is 20.0 wt % or 190.0-200.0 mg/ml. The initial particle size is from 0.4 to 2.0 microns. The micron dispersion of elemental boron in water is exposed to ultrasound for 10 minutes. The process is carried out using ultrasonic equipment with an output power of 25.0±0.05 kW and the ultrasonic vibration intensity of 1000.0 W/cm$^3$. The obtained composition contains particles <5 nm in size with a concentration of 180.0-185.0 mg/ml of nanoparticles in H$_2$O. The surface charge of boron nanoparticles is positive. The value of the ξ-potential is +10. The shape of the particles is irregular with sharpened edges. The stability of the composition over time is less than 96 hours.

Since the main effect of the resulting compositions is aimed at cancer therapy under neutron irradiation, biological tests were carried out to determine the toxicity, boron accumulation and the effectiveness of BNCT.

The studies were carried out with the formulations described in examples 1-20. Model experiments were performed on human U251, U87, and T98 and animal F98, C6, GL261 malignant glioma cell lines.

After incubation of cells with boron nanoparticles, quantitative analysis of boron content in cells was carried out by atomic emission spectroscopy in inductively coupled plasma.

Cytotoxicity data showed low toxicity of nanoparticles in the therapeutic range of boron concentration above 30 μg/g-tissue (or g-cell mass), which confirmed the suitability of nanoparticles for further irradiation experiments.

Experimental preclinical BNCT application close to real clinical conditions using synthesized compositions containing boron nanoparticles was carried out at an accelerator-based neutron source at the Budker Institute of Nuclear Physics SB RAS in Novosibirsk. At present, at the Institute of Nuclear Physics, a facility based on a new type of a charged particle accelerator—a tandem accelerator with vacuum insulation has been proposed, created and is under operation. At the facility, generation of neutrons and formation of an epithermal neutron flux are realized. It has been found that neutron irradiation of tumor cells, pre-incubated in a medium with boron nanoparticles, leads to a significant suppression of their viability. Irradiation of mice inoculated with a human glioblastoma leads to their complete recovery.

The invention claimed is:

1. A method of obtaining a composition for boron neutron capture therapy of malignant tumors comprising boron nanoparticles with particle size less than 100 nm, the method comprising:

i) placement of an elemental boron powder in water; and
ii) treatment of the elemental boron powder in water with ultrasound with a vibration intensity of between 1 W/cm$^3$ and 1000 W/cm$^3$ and an output power of more than 100 W, wherein the treatment with ultrasound is performed for a period of between 0.5 minutes and 800 minutes to obtain a composition for boron neutron capture therapy of malignant tumors.

2. The method of claim 1, further comprising adding to the elemental boron powder in water a water-soluble inorganic metal salt with an oxidation state of +1 or a mixture thereof before step ii) or during step ii).

3. The method of claim 2, wherein the weight ratio of the elemental boron powder to the salt or to the mixture of salts is between 1:0.01 and 1:30.

4. The method of claim 2, wherein the water-soluble inorganic metal salt is selected from chloride, nitrate, sulfate, sulfite, and a mixture thereof.

5. The method of claim 4, wherein the chloride is selected from sodium, potassium, lithium chloride, and a mixture thereof.

6. The method of claim 1, further comprising adding one or more stabilizers to the composition.

7. The method of claim 6, wherein the one or more stabilizers are selected from organic metal salts or their mixtures, inorganic metal salts with an oxidation state equal to or greater than +2, and compounds selected from blood plasma proteins, antibodies, hormones, E400-E499 additives, polysaccharides, fatty acids, proteins of vegetable origin, amino acid derivatives that are 1-amino-3-cyclobutane-1-carboxylic acid and 1-amino 3-cyclopentanecarboxylic acid, phenylalanine, linear and cyclic peptides, purines, pyrimidines, thymidines, nucleosides and nucleotides that are 3-carboranyl thymidine analogs, porphyrins, pluronics, polyhydric alcohols, polyethylene glycol, polyvinylpyrrolidone, polyvinyl alcohol, and synthetic polyamino acids.

8. The method of claim 6, wherein the one or more stabilizers are selected from citrates and acetates.

9. The method of claim 1, wherein the elemental boron powder is selected from amorphous boron powder, coarse-crystalline boron powder, fine-crystalline boron powder, and mixtures thereof.

10. A method of obtaining a composition for boron neutron capture therapy of malignant tumors comprising boron nanoparticles with particle size less than 100 nm, the method comprising:
i) placement of an elemental boron powder in water;
ii) treatment of the elemental boron powder in water with ultrasound with a vibration intensity of between 1 W/cm$^3$ and 1000 W/cm$^3$ and an output power of more than 100 W, wherein the treatment with ultrasound is performed for a period of between 30 and 300 minutes to obtain an intermediate composition;
iii) taking an upper part of the intermediate composition in a volume of less than 50 vol. % of the total volume of the composition; and
iv) treating the composition of step iii) with ultrasound with a vibration intensity of between 1 W/cm$^3$ and 1000 W/cm$^3$ and an output power of more than 100 W, wherein the treating with ultrasound is performed for a period of between 250 and 300 minutes to obtain a composition for boron neutron capture therapy of malignant tumors.

11. The method of claim 10, further comprising adding to the elemental boron powder in water a water-soluble inorganic metal salt with an oxidation state of +1 or a mixture thereof before or during step ii) or step iv).

12. The method of claim 11, wherein the weight ratio of the elemental boron powder to the salt or to the mixture of salts is between 1:0.01 and 1:30.

13. The method of claim 11, wherein the water-soluble inorganic metal salt is selected from chloride, nitrate, sulfate, sulfite, and a mixture thereof.

14. The method of claim 13, wherein the chloride is selected from sodium, potassium, lithium chloride, and a mixture thereof.

15. The method of claim 10, further comprising adding one or more stabilizers to the final composition.

16. The method of claim 15, wherein the one or more stabilizers are selected from organic metal salts or their mixtures, inorganic metal salts with an oxidation state equal to or greater than +2, and compounds selected from blood plasma proteins, antibodies, hormones, E400-E499 additives, polysaccharides, fatty acids, proteins of vegetable origin, amino acid derivatives that are 1-amino-3-cyclobutane-1-carboxylic acid and 1-amino-3-cyclopentanecarboxylic acid, phenylalanine, linear and cyclic peptides, purines, pyrimidines, thymidines, nucleosides and nucleotides that are 3-carboranyl thymidine analogs, porphyrins, pluronics, polyhydric alcohols, polyethylene glycol, polyvinylpyrrolidone, polyvinyl alcohol, and synthetic polyamino acids.

17. The method of claim 16, wherein the one or more stabilizers are selected from citrates and acetates.

18. The method of claim 10, wherein the elemental boron powder is selected from amorphous boron powder, coarse-crystalline boron powder, fine-crystalline boron powder, or mixtures thereof.

* * * * *